(12) United States Patent
Sheppard, Jr. et al.

(10) Patent No.: US 8,403,907 B2
(45) Date of Patent: Mar. 26, 2013

(54) METHOD FOR WIRELESSLY MONITORING IMPLANTED MEDICAL DEVICE

(75) Inventors: Norman F. Sheppard, Jr., New Ipswich, NH (US); John T. Santini, Jr., North Chelmsford, MA (US); Michael J. Cima, Winchester, MA (US); Robert S. Langer, Newton, MA (US); Dennis Ausiello, Wellesley Hill, MA (US)

(73) Assignee: MicroCHIPS, Inc., Waltham, MA (US)

( * ) Notice: Subject to any disclaimer, the term of this patent is extended or adjusted under 35 U.S.C. 154(b) by 951 days.

(21) Appl. No.: 11/926,458

(22) Filed: Oct. 29, 2007

(65) Prior Publication Data

US 2008/0221555 A1    Sep. 11, 2008

Related U.S. Application Data

(60) Continuation of application No. 11/747,598, filed on May 11, 2007, now abandoned, which is a division of application No. 09/975,672, filed on Oct. 10, 2001, now Pat. No. 7,226,442.

(60) Provisional application No. 60/239,222, filed on Oct. 10, 2000.

(51) Int. Cl.
    *A61M 31/00*    (2006.01)
(52) U.S. Cl. .................... 604/502; 604/890.1
(58) Field of Classification Search .... 604/890.1–892.1, 604/65–67, 131, 151–155, 500–522
    See application file for complete search history.

(56) References Cited

U.S. PATENT DOCUMENTS

| | | | |
|---|---|---|---|
| 3,692,027 A | 9/1972 | Ellinwood, Jr. | |
| 4,360,019 A | 11/1982 | Portner et al. | |
| 4,507,115 A | 3/1985 | Kambara et al. | |
| 4,564,363 A * | 1/1986 | Bagnall et al. | 604/891.1 |
| 4,585,652 A | 4/1986 | Miller et al. | |
| 4,731,049 A | 3/1988 | Parsi | |
| 4,793,825 A | 12/1988 | Benjamin et al. | |
| 4,865,813 A | 9/1989 | Leon | |
| 5,042,975 A | 8/1991 | Chien et al. | |
| 5,167,625 A | 12/1992 | Jacobsen et al. | |
| 5,170,801 A | 12/1992 | Casper et al. | |
| 5,200,051 A | 4/1993 | Cozzette et al. | |
| 5,252,294 A | 10/1993 | Kroy et al. | |
| 5,279,607 A * | 1/1994 | Schentag et al. | 604/890.1 |

(Continued)

FOREIGN PATENT DOCUMENTS

| | | |
|---|---|---|
| DE | 19716683 | 6/1998 |
| WO | 93/03790 | 3/1993 |

(Continued)

OTHER PUBLICATIONS

U.S. Appl. No. 11/747,598, filed Oct. 29, 2007, Norman Sheppard.

(Continued)

*Primary Examiner* — Kevin C Sirmons
*Assistant Examiner* — Phillip Gray
(74) *Attorney, Agent, or Firm* — Sutherland Asbill & Brennan LLP (57) ABSTRACT

A method is provided for monitoring the status of a medical device implanted in a patient. The method includes the steps of implanting in a patient a medical device which comprises (i) a substrate in which two or more reservoirs are located, with each covered by a reservoir cap, (ii) a drug or sensor located in the reservoir, (iii) a power source and actuation electronics for disintegrating or permeabilizing the reservoir cap, and (iv) a telemetry system; and then using said telemetry system to wirelessly transmit to a remote controller data about the condition of the power source and/or data about which reservoirs have been or have yet to be activated to release the drug therefrom or to expose the sensor therein.

9 Claims, 3 Drawing Sheets

U.S. PATENT DOCUMENTS

| | | | |
|---|---|---|---|
| 5,318,557 A | 6/1994 | Gross | |
| 5,324,316 A | 6/1994 | Schulman et al. | |
| 5,336,213 A | 8/1994 | D'Angelo et al. | |
| 5,366,454 A | 11/1994 | Currie et al. | |
| 5,368,588 A | 11/1994 | Bettinger | |
| 5,368,704 A | 11/1994 | Madou et al. | |
| 5,380,272 A | 1/1995 | Gross | |
| 5,429,822 A | 7/1995 | Gresser et al. | |
| 5,443,508 A | 8/1995 | Giampapa | |
| 5,474,527 A | 12/1995 | Bettinger | |
| 5,493,177 A | 2/1996 | Muller et al. | |
| 5,504,026 A | 4/1996 | Kung | |
| 5,585,069 A | 12/1996 | Zanzucchi et al. | |
| 5,662,689 A | 9/1997 | Elsberry et al. | |
| 5,713,954 A | 2/1998 | Rosenberg et al. | |
| 5,797,898 A | 8/1998 | Santini, Jr. et al. | |
| 5,798,042 A | 8/1998 | Chu et al. | |
| 5,807,397 A | 9/1998 | Barreras | |
| 5,841,122 A | 11/1998 | Kirchhoff | |
| 5,842,787 A | 12/1998 | Kopf-Sill et al. | |
| 5,843,767 A | 12/1998 | Beattie | |
| 5,949,187 A | 9/1999 | Xu et al. | |
| 5,962,081 A | 10/1999 | Ohman et al. | |
| 5,971,931 A | 10/1999 | Raff | |
| 5,976,336 A | 11/1999 | Dubrow et al. | |
| 5,989,445 A | 11/1999 | Wise et al. | |
| 6,001,090 A | 12/1999 | Lenhart | |
| 6,047,214 A | 4/2000 | Mueller et al. | |
| 6,051,017 A | 4/2000 | Loeb et al. | |
| 6,081,736 A | 6/2000 | Colvin et al. | |
| 6,096,656 A | 8/2000 | Matzke et al. | |
| 6,123,861 A | 9/2000 | Santini, Jr. et al. | |
| 6,129,685 A | 10/2000 | Howard, III | |
| 6,140,740 A | 10/2000 | Porat et al. | |
| 6,161,047 A | 12/2000 | King et al. | |
| 6,171,850 B1 | 1/2001 | Nagle et al. | |
| 6,178,349 B1 | 1/2001 | Kieval | |
| 6,185,455 B1 | 2/2001 | Loeb et al. | |
| 6,214,032 B1 | 4/2001 | Loeb et al. | |
| 6,243,608 B1 | 6/2001 | Pauly et al. | |
| 6,289,237 B1 | 9/2001 | Mickle et al. | |
| 6,319,241 B1 | 11/2001 | King et al. | |
| 6,334,859 B1 | 1/2002 | Richter | |
| 6,349,232 B1 | 2/2002 | Gordon | |
| 6,384,353 B1 | 5/2002 | Huang et al. | |
| 6,436,853 B2 | 8/2002 | Lin et al. | |
| 6,480,730 B2 | 11/2002 | Darrow et al. | |
| 6,491,666 B1 | 12/2002 | Santini, Jr. et al. | |
| 6,527,762 B1 * | 3/2003 | Santini et al. | 604/890.1 |
| 6,537,256 B2 | 3/2003 | Santini, Jr. et al. | |
| 6,551,838 B2 | 4/2003 | Santini, Jr. et al. | |
| 6,587,719 B1 | 7/2003 | Barrett et al. | |
| 6,656,162 B2 | 12/2003 | Santini, Jr. et al. | |
| 6,669,683 B2 | 12/2003 | Santini, Jr. et al. | |
| 6,673,596 B1 | 1/2004 | Sayler et al. | |
| 6,730,072 B2 | 5/2004 | Shawgo et al. | |
| 6,733,485 B1 | 5/2004 | Whitehurst et al. | |
| 6,757,560 B1 | 6/2004 | Fischer et al. | |
| 6,773,429 B2 | 8/2004 | Sheppard et al. | |
| 6,808,522 B2 | 10/2004 | Richards et al. | |
| 6,849,463 B2 | 2/2005 | Santini, Jr. et al. | |
| 6,908,770 B1 | 6/2005 | McDevitt et al. | |
| 6,968,743 B2 | 11/2005 | Rich et al. | |
| 6,976,982 B2 | 12/2005 | Santini, Jr. et al. | |
| 7,010,345 B2 | 3/2006 | Hill et al. | |
| 7,041,130 B2 | 5/2006 | Santini et al. | |
| 7,052,488 B2 | 5/2006 | Uhland | |
| 7,070,590 B1 | 7/2006 | Santini et al. | |
| 7,070,592 B2 | 7/2006 | Santini et al. | |
| 2001/0053885 A1 | 12/2001 | Gielen et al. | |
| 2002/0038137 A1 | 3/2002 | Stein | |
| 2002/0055761 A1 | 5/2002 | Mann et al. | |
| 2002/0064841 A1 | 5/2002 | Klemic et al. | |
| 2002/0072784 A1 | 6/2002 | Sheppard, Jr. et al. | |
| 2002/0082665 A1 | 6/2002 | Haller et al. | |
| 2002/0107553 A1 | 8/2002 | Hill et al. | |
| 2002/0111601 A1 | 8/2002 | Thompson | |
| 2002/0143369 A1 | 10/2002 | Hill et al. | |
| 2002/0144548 A1 | 10/2002 | Cohn et al. | |
| 2002/0165586 A1 | 11/2002 | Hill et al. | |
| 2003/0004549 A1 | 1/2003 | Hill et al. | |
| 2004/0106953 A1 * | 6/2004 | Yomtov et al. | 607/3 |
| 2004/0143236 A1 | 7/2004 | Santini, Jr. et al. | |
| 2004/0166140 A1 | 8/2004 | Santini, Jr. et al. | |
| 2005/0124979 A1 | 6/2005 | Santini, Jr. et al. | |
| 2005/0149000 A1 | 7/2005 | Santini, Jr. et al. | |
| 2006/0171888 A1 | 8/2006 | Santini, Jr. et al. | |
| 2006/0189963 A1 | 8/2006 | Santini, Jr. et al. | |

FOREIGN PATENT DOCUMENTS

| | | |
|---|---|---|
| WO | 99/42039 | 8/1999 |
| WO | 01/28629 | 4/2001 |
| WO | 01/37926 | 5/2001 |

OTHER PUBLICATIONS

U.S. Appl. No. 11/927,316, filed Oct. 29, 2007, Norman Sheppard.

Barillaro, et al., Optical Materials, 17(1-2):91-94 (2001).

Kano & Ikeda, "Fundamentals and practices of mediated bioelectrocatalysis," Analytical Sci., 16(10):1013-21 (2000).

Liu C., et al. "Applications of microfabrication and micromachining techniques to biotechnology," Trends in Biotechnology, vol. 15, No. 6, pp. 213-216.

Low, et al., "Microactuators Towards Microvalves for Responsive Controlled Drug Delivery," Sensors & Actuators B 67: 149-60 (2000).

Madou, Fundamentals of Microfabrication, pp. 468-512 (CRC Press 1997).

Madou & Florkey, "From Batch to Continuous Manufacturing of Microbiomedical Devices," Chem. Rev., 100: 2679-92 (2000).

Madou & He, "Expliotation of a Novel Artificial Muscle for Controlled Drug Delivery," pp. 495-497 (1999).

Palmore & Whitesides, "Microbial and Enzymatic Biofuel Cells," Enzymatic Conversion of Biomass for Fuel Prodcution, ACS Symposium Series 566:271-90 (1994).

Reynaerts, et al. "An Implantable drug-delivery system based on shape memory alloy micro-actuation", Sensors and Actuators A, 61(1-3):455-162 (1997).

Surbled, et al., "Array of Shape Memory Alloy One-Shot Micro-Valves for Drug Delivery," MME '99, Gif sur Yvette, France (Sep. 27-28, 1999).

Surbled, et al., "Shape Memory Alloys for Micromembranes Actuation," SPIE. 3825:63-70 (1999).

Tierney, et al., "New Electrorelease Systems Based on Microporous Membranes," J. Electrochem. Soc., 137:3789-3793 (1990).

Tierney, et al., "Electroreleasing Composite Membranes for Delivery of Insulin and Other Biomacromolecules," J. Electrochem. Soc., 137:2005-06 (1990).

Wilkinson, Autonomous Robots, 9(2): 99-111 (2000).

Wolf & Tauber, "Silicon Processing for the VLSI Era," (Lattice Press, 1986).

* cited by examiner

METHOD FOR WIRELESSLY MONITORING IMPLANTED MEDICAL DEVICE

CROSS-REFERENCE TO RELATED APPLICATIONS

This is a continuation of U.S. application Ser. No. 11/747,598, filed May 11, 2007, now pending, which is a divisional of U.S. application Ser. No. 09/975,672, filed Oct. 10, 2001, now U.S. Pat. No. 7,226,442, which claims priority benefit of U.S. Provisional Application No. 60/239,222, filed Oct. 10, 2000. These applications are incorporated herein by reference.

BACKGROUND OF THE INVENTION

This invention relates to miniaturized devices for the controlled exposure or release of molecules such as drugs and/or secondary devices such as sensors.

Microchip devices for chemical and drug delivery and for controlled exposure of reservoir contents have been described in detail in U.S. Pat. No. 5,797,898; U.S. Pat. No. 6,123,861 PCT WO 01/64344; and PCT WO 01/35928. One group of embodiments of these microchip devices provides active release or exposure of the contents of a reservoir in the substrate of the device. "Active" is used to refer to those embodiments in which release or exposure is initiated at a particular time by the application of a stimulus to the device or a portion of the device.

An important application for these active microchip devices is to serve as an implantable device for the delivery of drugs in the body of humans and animals, for the treatment or diagnosis of disease. Due to its small size, the microchip device may be implanted in the body in a variety of locations, including, but not limited to, under the skin and in the peritoneal cavity. The device may also be ingested for drug delivery or content exposure throughout the gastrointestinal tract. Flexibility of implant location and site variation are particularly important for example when local, rather than systemic, administration is desired. Currently available implantable drug delivery devices such as pumps may be too large for use in many of locations in the body.

U.S. Pat. No. 5,797,898 to Santini, et al., describes powering the active microchip devices using pre-charged power sources (e.g., pre-charged micro-batteries), which can be integrated with the microchip and its associated electronics. Such a pre-charged micro-battery can be a thin film battery fabricated on the microchip substrate itself, or it can exist as a separate component that is connected to the microchip substrate through interconnects and packaging. Such power sources generally must store all the power required during the operating lifetime of the microchip device. If it cannot store all of the required power during the intended useful life of the microchip device, then the depleted battery must be replaced with a new battery. However, such replacement typically is impractical or undesirable for an implanted device. It would therefore be advantageous to avoid the need for battery replacement. Furthermore, conventional means of powering an implantable device may be unsuitable for a variety of implanted devices, particularly for all possible implant locations.

U.S. Pat. No. 5,797,898 also describes incorporating a pre-programmed microprocessor into the active microchip device to control which reservoirs are activated and when they are activated. The microprocessor is disclosed as being fabricated onto the back of the microchip substrate. It would be advantageous to be able to alter the programming after implantation in order to make the microchip device more flexible and adaptable to various applications, particularly implant applications.

It is therefore an object of the present invention to provide devices and methods for reducing or eliminating the need for pre-charged power sources for active release microchip devices.

It is another object of the present invention to provide devices and methods for avoiding explantation of implanted microchip devices for the purpose of replacing or recharging the device's power source or for the purpose of reprogramming the device's microprocessor.

It is a further object of the present invention to provide additional means for powering and communicating with microchip drug delivery and sensing devices.

These and other objects, features, and advantages of the present invention will become apparent upon review of the following detailed description of the invention taken in conjunction with the drawings and the appended claims.

SUMMARY OF THE INVENTION

Devices, systems, and methods are provided for wirelessly powering and/or communicating with microchip devices used for the controlled exposure and release of reservoir contents, such as drugs, reagents, and sensors.

In a preferred embodiment, the system for the controlled release or exposure of reservoir contents comprises (1) a microchip device comprising a substrate having a plurality of reservoirs containing reservoir contents for release or exposure; and (2) a rechargeable or on-demand power source comprising a local component which can wirelessly receive power from a remote transmitter; wherein the received power can be used, directly or following transduction, to activate said release or exposure of the reservoir contents. These systems advantageously do not require a power storage unit to be physically connected to or integrated into the microchip device. For example, the local component can be adapted to receive power from an electromagnetic energy source, such as radio frequency signals or a laser, and/or from a sonic energy source, such as an ultrasound generator. The system optionally can include a rechargeable power storage unit, such as a capacitor or rechargeable battery. However, it need not store all of the power required for the operating life of the microchip, since additional power can wirelessly be transmitted and received when needed (i.e. on-demand). The rechargeable power storage unit can include, for example, a coil for the receipt of electromagnetic energy, a photocell, a hydrophone, or a combination thereof.

The system may further include actuation electronics, local controllers, and a telemetry system. Actuation electronics, such as multiplexers/demultiplexers, selectively control and direct the power to selectively open the reservoirs. The local controller can control the actuation electronics, and may include microprocessors, read only memory, random access memory, clocks, analog input/output devices, digital input/output devices, programmable logic circuits, and combinations thereof. A telemetry system wirelessly transfers data (e.g., a signal) between the microchip device and a remote controller.

In another preferred embodiment, the system for the controlled release or exposure of reservoir contents comprises (1) a microchip device comprising a substrate a plurality of reservoirs containing reservoir contents for release or exposure; and (2) a telemetry system for the wireless transfer of data between the microchip device and a remote controller. The system can further comprise actuation electronics to selectively open the reservoirs, as well as a local controller (which typically would be in wireless communication with the remote controller of the telemetry system) for controlling the actuation electronics.

The data transfer can be accomplished using a first coil in the microchip device to inductively couple electromagnetic energy to a corresponding coil in the remote controller. Alternatively, the transfer may utilize various kinds of transmitters and receivers. For example, the microchip device can comprise a receiver which includes photocells, photodiodes, phototransistors, and/or ultrasonic receivers, where the remote controller comprises a light-emitting diode (LED), a laser, and/or an ultrasonic transmitter. For example, LED's can be fabricated on or in the microchip device, wherein the LED can be used to transmit energy or data to other components of the system, such as external/internal transmitters or remote controllers using light of varying wavelengths.

It should be noted that the wireless transmission of power and the wireless transmission of data can be transmitted to the microchip device in the same signal and then separated appropriately in the microchip device.

The microchip device systems can be used in a variety of applications. A preferred application is the controlled delivery of a drug, chemical reagent, or biosensor to sites within the body of a human or animal. In one example, the microchip device is adapted for implantation onto or in the eye of a human or animal, and the remote controller and/or power source comprises an ophthalmic laser. In another example, the microchip device is adapted for oral administration, and the remote controller comprises a radio frequency transmitter.

The system also has a variety uses that are not limited to implantation. For example, the reservoir contents may include a sensor for detecting a chemical or biological molecule at the site in which the microchip is placed, and the telemetry system transmits a status of the sensor detection to the remote controller. Such a site could be in vivo or in vitro. The chemical or biological molecule could, for example, be associated with a chemical or biological weapon, and the system used in an early warning/detection system.

In a preferred variation of the embodiments described above, each reservoir can have a reservoir cap positioned on the reservoir over the reservoir contents, wherein release or exposure of the reservoir contents is controlled by diffusion through or disintegration of the reservoir cap. The reservoir cap can be an anode, such that upon application of an electric potential between a cathode and the anode the reservoir cap is oxidized to facilitate its disintegration, thereby exposing the reservoir contents to a surrounding fluid.

The reservoir content preferably is a drug, a biosensor, or a combination thereof.

DETAILED DESCRIPTION OF THE INVENTION

Devices, systems, and methods have been developed for wirelessly powering and/or communicating with microchip devices used for the controlled exposure and release of reservoir contents, such as drugs, reagents, and sensors.

The Microchip Device Systems

The systems include a microchip device, along with means for wirelessly delivering power (i.e. energy) to the microchip device, means for wirelessly transferring data between the microchip device and a remote controller, or both means.

The Microchip Device

The microchip device is described in U.S. Pat. No. 5,797,898 and No. 6,123,861, both to Santini, et al., and PCT WO 01/64344, WO 01/41736, WO 01/35928, and WO 01/12157, which are hereby incorporated by reference in their entirety. Each microchip device includes a substrate having a plurality of reservoirs containing reservoir contents for release or exposure. In a preferred embodiment, each reservoir has a reservoir cap positioned on the reservoir over the reservoir contents, wherein release or exposure of the reservoir contents is controlled by diffusion through or disintegration of the reservoir cap. The reservoir cap can be an anode, such that upon application of an electric potential between a cathode and the anode the reservoir cap is oxidized to facilitate its disintegration, thereby exposing the reservoir contents to a surrounding fluid.

In another embodiment, the reservoir cap includes an electrically- or thermally-responsive polymer whose integrity or porosity can be modulated (i.e. increased or decreased) upon application of electrical energy to the reservoir cap (e.g., for the electrically responsive polymer) or to a nearby resistor (e.g., for the thermally responsive polymer). Similarly, the reservoir cap can include or be formed of a polymer having a porosity that can be modulated by application of electromagnetic energy, acoustic energy, or a particular chemical species (e.g., for chemical actuation) provided by the microchip device or other source.

The microchip reservoir contents can be essentially any chemical or miniature device. In a preferred embodiment, the chemical is a therapeutic, prophylactic, or diagnostic agent. (The term "drug" is used herein to refer any of these agents.) Preferred drug delivery applications include potent compounds, including both small and large (i.e. macro) molecules, such as hormones, steroids, chemotherapy medications, vaccines, gene delivery vectors, and some strong analgesic agents. An example of a diagnostic agent is an imaging agent such as a contrast agent. Other molecules that can be released include fragrances and flavoring agents.

The reservoir contents also can be catalyst (e.g., zeolites, enzymes), one or more reagents, or a combination thereof. In another embodiment, the reservoir content includes a secondary device such as a sensor and sensing component, e.g., a biosensor. Examples of sensing components include components utilized in measuring or analyzing the presence, absence, or change in a chemical or ionic species, electromagnetic or thermal energy (e.g., light), or one or more physical properties (e.g., pH, pressure) at a site. The contents may either be released from or remain immobilized in the reservoir, depending on the particular application. Individual reservoirs may contain multiple types of chemicals, multiple types of devices, or combinations of devices and chemicals.

The microchip devices can be made and assembled using microfabrication methods own in the art, particularly those methods described and referenced in U.S. Pat. No. 5,797,898 and No. 6,123,861, both to Santini, et al., and in PCT WO 01/64344, WO 01/41736, WO 01/35928, and WO 01/12157.

Wireless Powering Means/On-Demand Power Sources

Means of supplying power to active-release microchip devices include the use of a precharged power source (which contain all of the power required for operation over the life of the microchip device), a source that can be periodically recharged, and an on-demand power source. The latter two power sources are preferred.

The microchip device typically includes a transducer for receiving energy wirelessly transmitted to the device, circuitry for directing or converting the received power into a form that can be used or stored, and if stored, a storage device, such as a rechargeable battery or capacitor. Therefore in preferred embodiments, the system for the controlled release or exposure of reservoir contents includes a microchip device and a rechargeable or on-demand power source. The on-demand power source advantageously does not require that a power storage unit to be physically connected to or integrated into the microchip device. The rechargeable power source (i.e. the rechargeable power storage unit) can store power, but advantageously need not store all of the power required for the operating life of the microchip. The rechargeable power source and on-demand power sources can both be included in a single microchip device, as it is common for a system having an on-demand power source to include a power storage unit, such as a capacitor or battery.

The systems described herein preferably are provided with a means for monitoring the state of any power storage unit. As power is used or depleted from the storage device, additional power can wirelessly be transmitted to and received by the rechargeable power storage unit when needed. Rechargeable power sources provide a means of extending the operating life of the microchip device beyond that possible with pre-charged storage cells or non-rechargeable systems.

Systems and techniques for on-demand power by wireless transmission, which can be adapted for use with the microchip devices described herein, are disclosed, for example, in U.S. Pat. No. 6,047,214 to Mueller, et al.; U.S. Pat. No. 5,841,122 to Kirchhoff; U.S. Pat. No. 5,807,397 to Barreras; and U.S. Pat. No. 5,324,316. The systems typically involve a receiver and a transmitter of one or more forms of energy. The rechargeable or on-demand power source preferably includes a local component which can wirelessly receive power from a remote transmitter. As used herein, the term "local" refers to being local to the microchip device (rather than remote), and includes, but is not limited to, having the local component attached to the microchip device, such as by fabrication onto the substrate.

The local component can be adapted to receive power by a variety of means. For example, the local component can be adapted to receive power from an electromagnetic (EM) energy source, or an acoustic (i.e. sonic) energy or other mechanical energy source. Electromagnetic energy refers to the full spectral range from x-ray to infrared. Representative examples of useful EM energy forms include radio frequency signals and laser light. A representative example of a useful form of acoustic energy is ultrasound. In various embodiments, the rechargeable power storage unit can include, for example, a coil for the receipt of electromagnetic energy, or a means for transducing other types of energy, such as a photocell, a hydrophone, or a combination thereof. Additional components may include a means of power conversion such as a rectifier, a power storage unit such as a battery or capacitor, and an electric potential/current controller (i.e. potentiostat/galvanostat).

The microchip device also can include a component to convert mechanical or chemical energy from the body of the human or animal into power (i.e. energy) which can be used to activate release or exposure of the reservoir contents. For example, components comprising accelerometers and gyroscopes, can be used to convert motion of a body into electrical energy. Similarly, an implanted transducer can convert heartbeats into useful energy, as currently is done with some pacemaker designs. See, e.g., U.S. Pat. No. 5,713,954. In another embodiment power is generated/converted from a chemical energy source. For example, the microchip can comprises a biofuel cell which generates the power by chemically reacting a molecule present in the body. Examples of these fuel cells are described for example in Palmore & Whitesides, "Microbial and Enzymatic Biofuel Cells," *Enzymatic Conversion of Biomass for Fuel Production*, ACS Symposium Series 566: 271-90 (1994); Kano & Ikeda, "Fundamentals and practices of mediated bioelectrocatalysis," *Analytical Sci.*, (16(10):1013-21 (2000); and Wilkenson, *Autonomous Robots*, 9(2): 99-111 (2000). In a typical embodiment, the implanted device would have an immobilized enzyme which would react with a biological molecule to cause electron transfer, thereby causing an electric current to flow. Possible useful biological molecules include triphosphates, such as ATP, and carbohydrates, such as sugars, like glucose.

Many of these components (except for the external energy transmission source) may be fabricated on the microchip ("on-chip" components) using known MEMS fabrication techniques, which are described, for example, in Madou, *Fundamental of Microfabrication* (CRC Press, 1997) or using known microelectronics processing techniques, which are described, for example, in Wolf & Tauber, *Silicon Processing for the VLSI Era* (Lattice Press, 1986). Each of these components (except the external energy transmission source) also may exist as discrete, "off the shelf" microelectronic components that can be connected to the microchip devices through the use of hybrid electronic packaging or multi-chip modules (MCMs). An active-release microchip device with the capability of receiving power through wireless means also can be composed of a combination of "on-chip" components and "off the shelf" components.

The particular power needs of the microchip device will depend on the application for and the specific design of the microchip device. Examples of design factors include the size requirements and anticipated operating life of the device. The particular devices and techniques for transmitting power will likely depend on the selected sites for the microchip device and remote transmitter. For example, for an implanted microchip, the body tissue will affect the transmission of power from an externally located transmitter. For example, inductively coupled electromagnetic energy typically penetrates body tissues to a limited extent; however, sonic energy, e.g., ultrasound, is readily transmitted through tissue and bodily fluids. As another example, although light (e.g., visible light) is generally not transmitted through tissue, it may be easily transmitted through the aqueous and vitreous humor of the eye. However, other electromagnetic radiation, for example x-rays, may readily be transmitted through tissue, depending primarily upon the wavelength of the radiation.

In one form, the system provides remote recharging of a battery for powering a microchip device.

In one embodiment having an in vivo rechargeable power storage unit, the power storage unit is separate from the other in vivo electronic components and communicates with them by wire or by in vivo telemetry. See for example, the implantable heart apparatus and energy transfer systems described in PCT WO 01/37926 and WO 01/28629.

The system may further include a telemetry system to wirelessly transfers data (e.g., a signal) between the microchip device and a remote controller or between components of the microchip device.

Wireless Communication Means/Telemetry System

Means for sending and receiving data using wireless technology are similar to those described for the wireless transmission of power. In a preferred embodiment, the system for the controlled release or exposure of reservoir contents includes a microchip device and a telemetry system for the wireless transfer of data between the microchip device and a remote controller. Generally, the telemetry system includes a transmitter and a receiver. A transmitter can be included in the remote controller, the microchip device, or both when data is transferred in both directions (to/from the microchip device), when the receiver is included in the microchip device, the remote controller, or both, respectively. As used herein, the "remote controller" therefore can include a transmitter, a receiver, or both.

Generally, the telemetry (i.e. the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry means also may be used. Examples include optical communication, where the receiver is in the form of a photocell, photodiode, and/or phototransistor, and where the transmitter a light-emitting diode (LED) or laser. For example, an LED could be fabricated into the silicon microchip substrate, either inside or outside of the reservoirs, by using or adapting techniques such as those described in Barillo, et al., "A porous silicon LED based on a standard BCD technology", *Optical Materials* 17(1-2):91-94 (2001). Optical telemetry techniques are further described, for example, in U.S. Pat. No. 6,243,608. For telemetry through soft tissue of the body, acoustic (i.e. sonic) energy, such as ultrasound energy, may be used as a means of communication. See, e.g., U.S. Pat. No. 6,140,740. One skilled in the art can adapt these known telemetry means for use with a microchip device to optimize power and data exchange. For example, one can account for impedance matching with tissue and receptive field and other factors for optimizing ultrasound transmission.

In various embodiments, the microchip device is provided with a receiver that accepts commands and data from the remote controller, and may be used to actuate a reservoir, to request status information about the state of the system or an event log, or to reprogram the controller operating system (e.g., the internal firmware). In an embodiment in which the microchip device is implanted in a human or animal, the remote controller can include a means of display and/or actuation that can be used by the physician or patient to operate and monitor the microchip device. For example, the microchip may wirelessly transmit to a remote controller, comprising a receiver, information about the battery condition and the location and number of reservoirs used and remaining. Additional support circuitry may be used to interface to biosensors or other types of devices such as pacemakers or defibrillators.

Other Components and Features of the Systems

It should be noted that the wireless transmission of power and the wireless transmission of data can be transmitted to the microchip device in the same signal and then separated appropriately in the microchip device.

The systems described herein may further include actuation electronics and local controllers. Actuation electronics selectively control and direct the power to the desired reservoirs. The actuation electronics contains circuitry to condition the power in a form that is needed for opening the reservoirs. For example, this circuitry may include signal generators/oscillators, voltage or current sources, amplifiers, and/or switches. For metal film reservoir caps, the actuation electronics preferably includes a potentiostat. Representative types of actuation electronics include potentiostat/voltage sources, galvanostat/current sources, multiplexers, and demultiplexers. In a preferred embodiment, the actuation electronics preferably includes a demultiplexer to route the power to the desired reservoirs. The demultiplexer may be integrated on the microchip or may be a separate chip or electrical component.

The local controller can control the actuation electronics and typically is responsible for operation of the device. The complexity of the controller will depend on the particular application of the microchip. The controller generally is either a microprocessor-based system or a dedicated logic circuit with a finite number of operational states. In the case of a microprocessor system, there preferably is a microprocessor, memory (read-only and random-access), clock, analog input/output devices, and digital input/output devices. The memory generally will contain a set of instructions to be executed by the microprocessor. These instructions can include routines to actuate the reservoirs, to receive commands or data from the remote controller, to transmit information to the remote controller, and to measure and interpret signals from devices such as sensors. A controller based on a dedicated logic circuit may be controlled by the receipt of commands or data in the form of an encoded (voltage) signal. See, e.g., U.S. Pat. No. 5,324,316, which describes using a dedicated logic circuit as a controller of an implantable microstimulator. The components of the controller system may be integrated as part of the microchip on the same substrate, or may be separate local components.

Use of the Microchip Devices and Systems

The microchip device systems can be used in a wide variety of applications. The applications can be ex vivo or in vitro, but more preferably are for in vivo applications, particularly following non- or minimally-invasive implantation.

Preferred applications for using the devices and systems include the controlled delivery of a drug (i.e. a therapeutic, prophylactic, or diagnostic agent) to sites within the body of a human or animal, biosensing, or a combination thereof. The microchip systems are especially useful for drug therapies in which it is desired to control the exact amount, rate, and/or time of delivery of the drug. Preferred drug delivery applications include the delivery of potent compounds, including both small and large molecules, such as hormones, steroids, chemotherapy medications, vaccines, gene delivery vectors, and some strong analgesic agents.

The microchips can be implanted via surgical procedures or injection, or swallowed, and can deliver many different drugs, at varying rates and varying times. In one example, the microchip device is adapted for implantation onto or in the eye of a human or animal, and the remote controller comprises an ophthalmic laser. In another example, the microchip device is adapted for oral administration, and the remote controller comprises a radio frequency transmitter.

In another preferred embodiment, the microchip device includes one or more biosensors (which may be sealed in reservoirs until needed for use) that are capable of detecting and/or measuring signals within the body of a patient. As used herein, the term "biosensor" includes, but is not limited to, sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as blood gases, drug concentration, or temperature.

The system also has a variety uses that are not limited to implantation. For example, the reservoir contents may include a sensor for detecting a chemical or biological molecule at the site in which the microchip is placed, and the telemetry system transmits a status of the sensor detection to the remote controller. Such a site could be in vivo or in vitro. The chemical or biological molecule could, for example, be associated with a chemical or biological weapon, and the system used in an early warning/detection system.

Active microchip devices may be controlled by local microprocessors or remote control. Biosensor information may provide input to the controller to determine the time and type of activation automatically, with human intervention, or a combination thereof. The microchip devices have numerous in vivo, in vitro, and commercial diagnostic applications. The microchips are capable of delivering precisely metered quantities of molecules and thus are useful for in vitro applications, such as analytical chemistry and medical diagnostics, as well as biological applications such as the delivery of factors to cell cultures.

The present invention can best be understood with reference to the following non-limiting examples.

Example 1

Chemical Releasing Microchip with Electrochemical Actuation and RF Power Transmission An electrochemically actuated microchip device having reservoirs covered by thin film gold reservoir caps can be fabricated using the processes described in U.S. Pat. No. 6,123,861. The reservoirs contain drug or other molecules for release. Application of an electric potential of approximately 1.0 volt (with respect to a saturated calomel reference electrode) in the presence of chloride ions would cause the reservoir caps to oxide and disintegrate, releasing the material stored in the reservoir. An on-demand power and control system would include an RF generating and a transmission source in an external controller unit. The microchip device would include a receiver coil (i.e. an inductor), an optional power converter (rectifier, regulator), a power storage unit (e.g., a capacitor, micro-battery), optional potentiostat or galvanostat circuitry (if electric potential or current modulation is required), a demultiplexer, a timer, and a microprocessor.

When release from a particular reservoir is desired, an RF signal is (wirelessly) transmitted to the reservoir-containing microchip device. The RF signal would induce an AC electric current in the receiver coil. This RF generated AC current can be rectified to DC current and directed to a unit for power storage, or if the electric current/corrosion behavior of the reservoir cap is well characterized, then the current can be sent directly to the anode reservoir cap covering the particular reservoir from which release is desired. In some cases, the received power is directed through a galvanostat or potentiostat to modulate the current or to produce a specific electric potential (relative to a reference electrode) at the reservoir cap. The electric current or potential is directed to the correct reservoir by a microprocessor-controlled demultiplexer. The microprocessor can be coupled with memory and a timer to enable timed dose regimens to be stored on-chip. The microprocessor then can direct power from the power storage unit or directly from the AC to DC converter to the correct reservoir in a particular release pattern programmed into the memory.

The release pattern also could be controlled in a wireless manner via commands sent from a remote controller over a telemetry system. Alternatively, the delivery of the drug or other molecule could be controlled by feedback from a biosensor located on or near the microchip, and interfaced to the controller.

Figure 1:
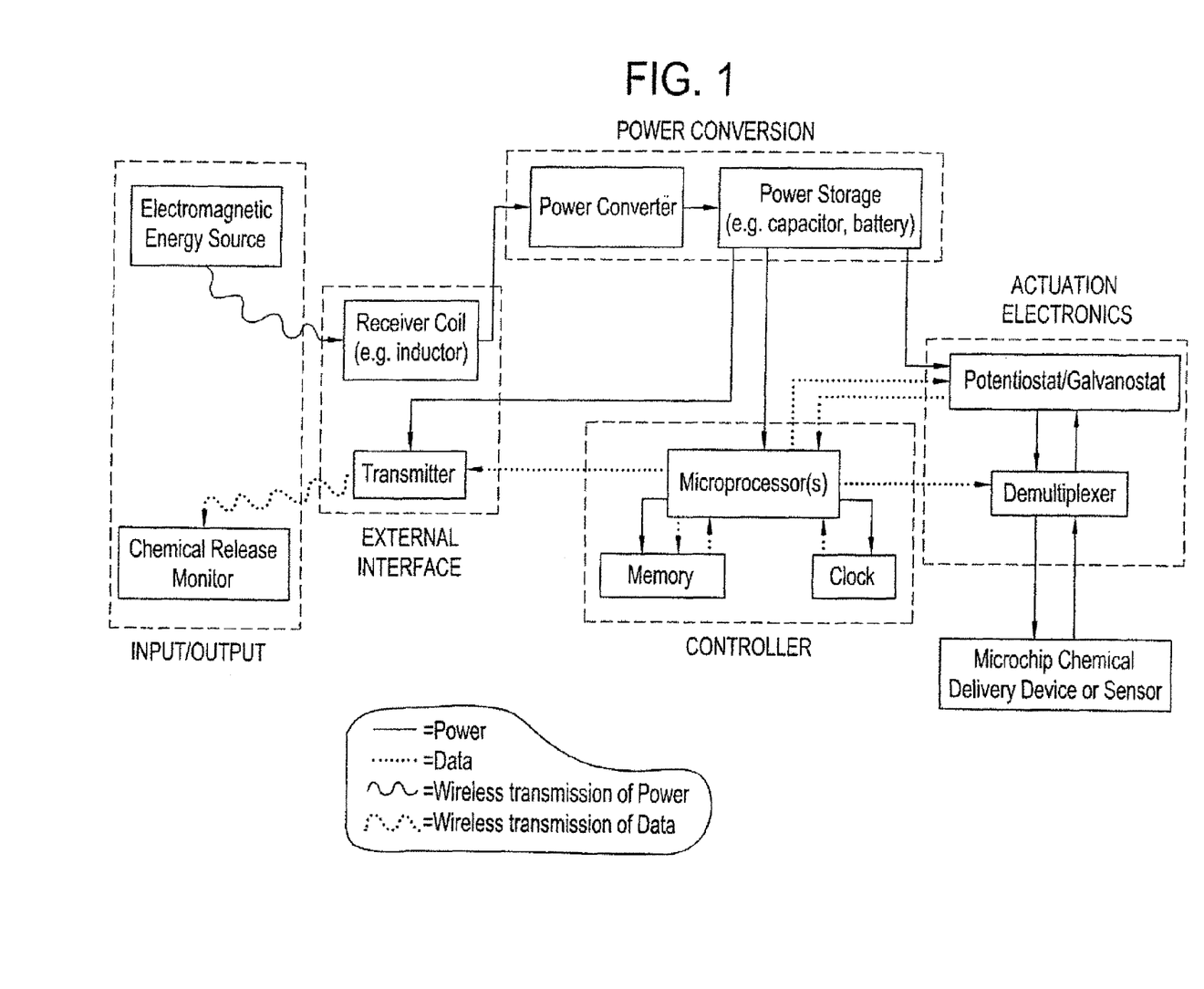
FIG. 1 is a schematic showing the primary components of a system for the wireless transmission of power or data to or from a microchip device for the release or exposure of reservoir contents.

This example may be better understood with reference to FIG. 1, which is a schematic that illustrates the primary components and the flow of power and data in a typical wireless microchip system.

Example 2

Microchip for the Selective Exposure of Reservoir Contents with Thermal Activation and RF Power Transmission A microchip device similar to that described in Example 1 can be made with reservoirs containing catalysts for reactions and/or sensors for chemical and biological agent detection, wherein power transmitted by wireless methods can be used to open the reservoirs to selectively expose the contents. In this embodiment, electromagnetic energy is transmitted to a receiver coil located on or connected to the microchip device. The induced AC current can be rectified to DC current to charge a storage battery or capacitor, or sent directly to resistors located on, near, or inside the reservoirs that are to be opened. Current passing through the resistor will cause a temperature rise in the resistor and surrounding area. The rise in temperature can cause the reservoir cap material to disintegrate, melt, or phase change and selectively expose the sensor or catalyst. Alternatively, a temperature rise inside the reservoir can result in a rise in pressure inside the reservoir that may cause the reservoir cap to rupture, exposing the contents of the reservoir to the surrounding environment. As in Example 1, the direction of the power to the proper reservoir is accomplished through the use of a demultiplexer controlled by a preprogrammed microprocessor, remote control, or biosensor.

Example 3

Microchip for Release of Drug to the Eye Using Laser Actuation

Lasers are used routinely in eye surgeries and other eye procedures for the treatment of conditions such as diabetic retinopathy, retinal detachments, age-related macular degeneration. Some conditions, notably macular degeneration, can be treated with periodic administration of medication delivered to the eye; however currently available means for doing so, such as injections, are difficult. To overcome such difficulties, an implantable microchip device can be provided to deliver doses of one or more types of medication to the eye on a periodic basis for an extended period of time. As the power requirements for electrochemically actuated silicon microchip devices with thin film gold reservoir caps are sufficiently small, the power can be wirelessly supplied, for example, via an ophthalmic laser. The ophthalmic laser also could be used to wirelessly communicate instructions to the implanted microchip device. Both power and data can be transmitted, for example, by modulating the signal that will carry the power; the modulation information to be communicated to the implanted microchip device.

Figure 2A:
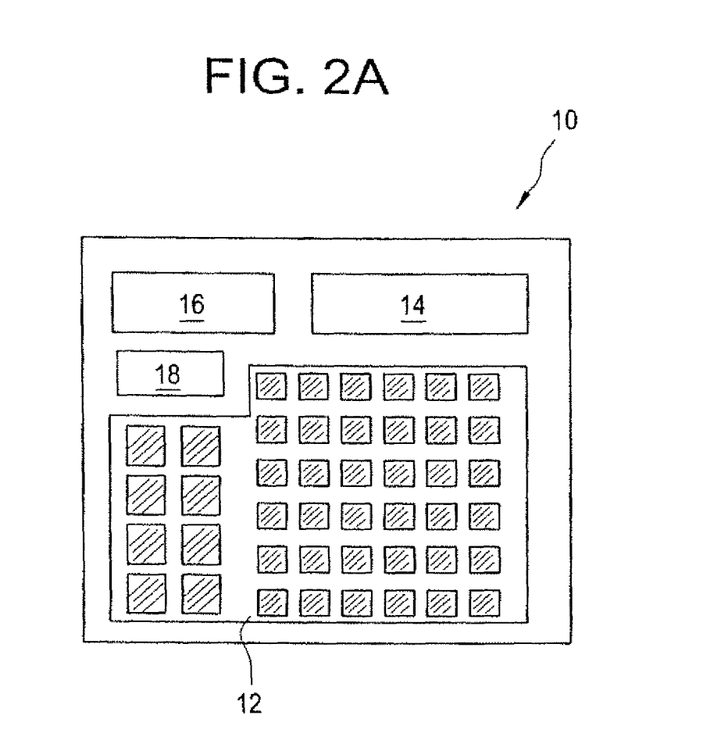
FIG. 2(a) illustrates one embodiment of a configuration of a microchip system for drug release into the eye that is equipped for power and data transmittal by laser.

Such an implantable wireless ocular delivery system would typically include (1) the drug-containing microchip with its local controller, external interfaces, power conversion electronics, and actuation electronics; and (2) the ophthalmic laser. The external interface and power conversion electronics typically would include a photocell to receive the incident light energy, circuitry to generate the needed voltage, storage means such as a capacitor or battery, and circuitry to decode information transmitted by modulating the laser input. The controller typically would be a microprocessor with associated support circuitry such as a memory and a clock, although a dedicated integrated circuit may work for some embodiments. Electronics required to actuate electrochemical microchips typically would include means for controlling the electrode potential, such as a potentiostat or galvanostat, and a demultiplexer to direct the potential to the desired reservoir. If desired, the system would provide feedback, for example, to confirm the successful delivery of a dose. This information could be transmitted back to the operator or to a computer monitoring system, either optically by using a light-emitting diode (LED) or by other modes of wireless transmission, such as RF. FIG. 2A illustrates one possible configuration of the microchip device configuration, wherein microchip device 10 includes an array of reservoirs 12 containing drug to be released, power conversion, actuation electronics and local controller area 14, photocell 16, LED or wireless telemetry transmitter 18.

Figure 2B:
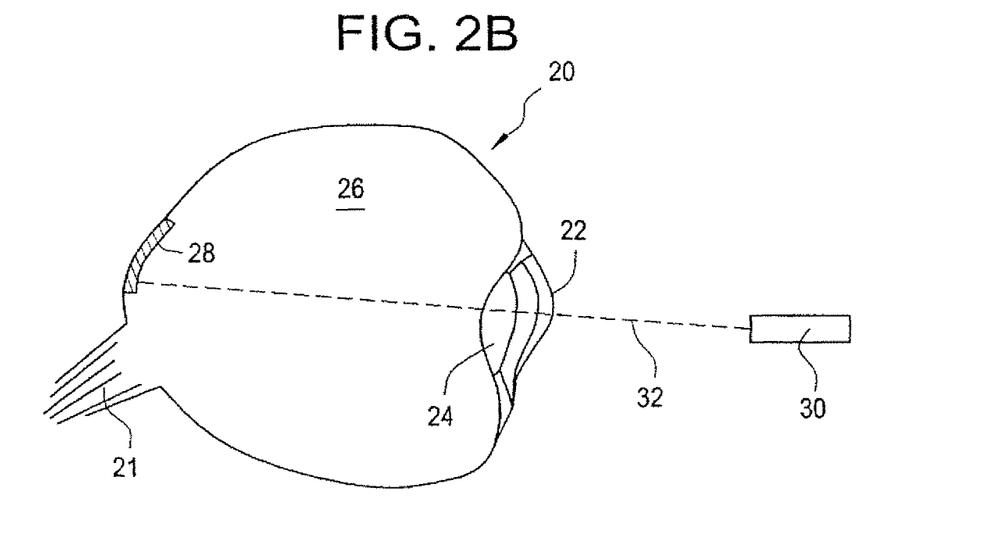
FIG. 2(b) illustrates a process of using an ophthalmic laser to transmit power and data to a drug delivery implant in the eye.

An ophthalmologist could initiate drug release and communication with eye-implanted microchips by directing an ophthalmic laser toward the appropriate portion of the microchip in the patient's eye. See FIG. 2B, which illustrates an eye 20 with optic nerve 21, wherein microchip device 28 is implanted at the back of the interior of the eye. An ophthalmic laser 30 directs power and data via laser light 32 through cornea 22, lens 24, and vitreous humor 26, to power and communicate with the implanted microchip device 28. Many ophthalmologists are already skilled in the use of such lasers, so these procedures could be readily performed.

Example 4

Orally Administered Microchips for Drug Delivery Having Proximity Actuation

A potential advantage of orally administered, drug delivery microchips or sensors is that they can be activated at a specific time or at a specific location in the gastrointestinal tract. Such control over the time and location of release can be achieved using pre-programmed microprocessors, remote control systems (e.g. wireless systems), or biosensors. One method of initiating drug release or exposure of a sensor at a particular location in the gastrointestinal tract would involve using a remote, wireless system of control that was highly location dependent. For example, a patient that just swallowed an orally administered microchip could wear a small RF transmitter on their belt. The filed produced by the RF transmitter would be designed to localize the power at a specific location in the gastrointestinal tract. Multiple coils or antennas could be used to more precisely locate the field so that its signal could only be detected at the desired location. The microchip would travel through the gastrointestinal (GI) tract until it reached a position where it could detect the signal from the transmitter.

As in Example 1, the microchip would receive power from the RF transmitter and could release drug or expose internal sensors. The position of release or exposure in the gastrointestinal tract would be controlled by the nature of the signal coming from the RF transmitter (i.e. strength of signal), the positioning of the transmitter (for example, its position on the patient's belt), and the distance between the microchip and the transmitter (which is based on how far the microchip has traveled in the gastrointestinal tract).

Figure 3:
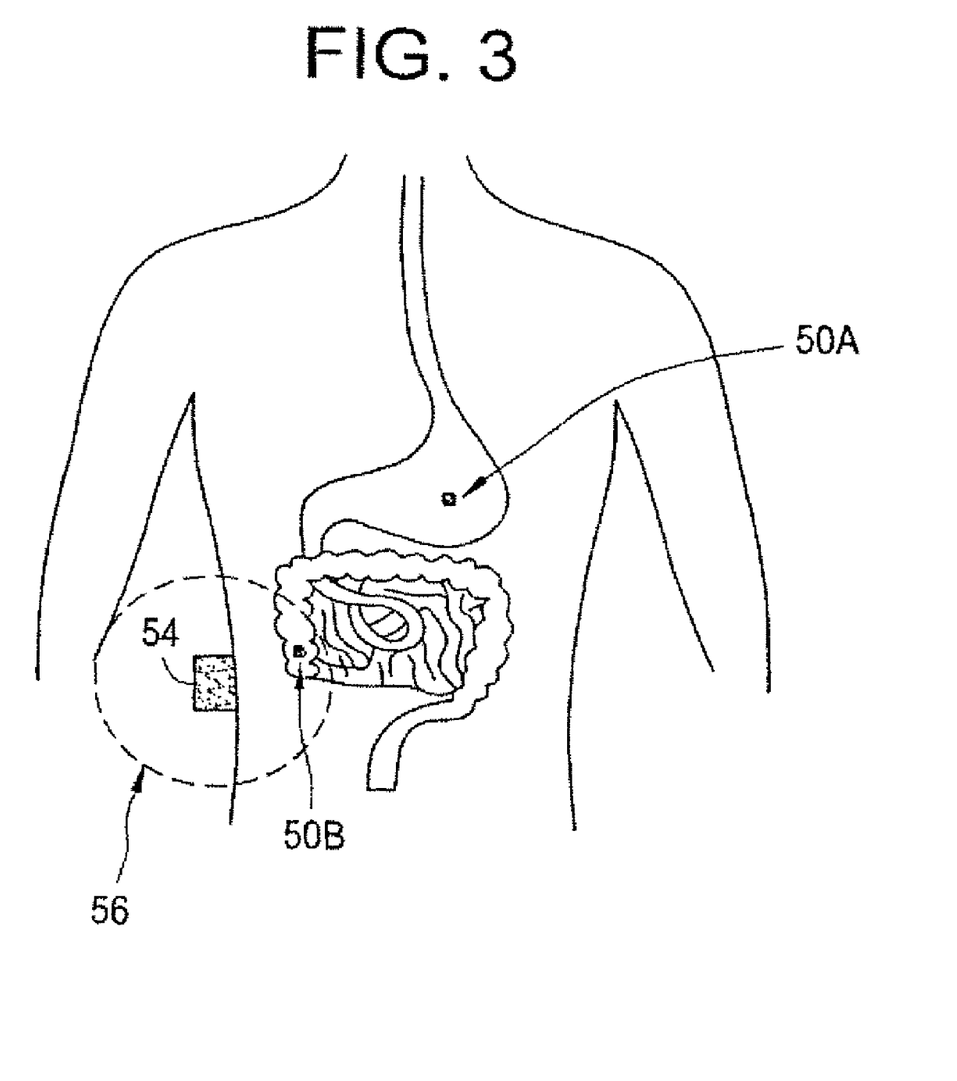
FIG. 3 is a diagram illustrating how a microchip device can be activated at a specific location in the gastrointestinal tract based on the location of a drug delivery microchip relative to an RF transmitter.

This process is illustrated in FIG. 3, which shows a microchip device 50A at a first location (i.e. the stomach) in the GI tract, the microchip device 50B at a second location (i.e. the colon), and RF transmitter 54 having an RF signal range shown by dashed line 56. As the device passes through the GI tract, it moves from position 50A, which is outside the RF signal range 56, to position 50B, which is inside RF signal range 56 and can be powered by the signal from RF transmitter 54.

Example 5

Microchips Designed to Minimize Medical Errors

The inclusion of a microprocessor, memory, and a timer also can help decrease the potential for drug overdoses or the administration of the wrong drugs to patients. Safety protocols can be stored in the memory and continuously checked by the microprocessor to prohibit (i) the release of too much drug to a patient over a particular time interval, and/or (ii) the simultaneous release of two or more incompatible drugs. In addition, the microchip can store in memory the exact amount of drug delivered, its time of delivery, and the amount of drug remaining in the microchip. This information can be transmitted using wireless technology (for implants) or using standard computer connections (for external, in-line, or intravenous systems) to the physician or to a central monitoring system on a real-time basis. This allows the physician to remotely monitor the patient's condition.

Modifications and variations of the methods and devices described herein will be obvious to those skilled in the art from the foregoing detailed description. Such modifications and variations are intended to come within the scope of the appended claims.

We claim:

1. A method for monitoring the status of a medical device implanted in a patient, the method comprising:
   implanting in a patient a medical device which comprises (i) a substrate in which two or more reservoirs are located, with each covered by a reservoir cap, (ii) a drug or sensor located in the reservoir, (iii) a power source and actuation electronics operable to melt each reservoir cap and thereby expose the drug or sensor to an environment at the site of implantation in the patient, and (iv) a telemetry system; and
   using said telemetry system to wirelessly transmit to a remote controller data about the condition of the power source and/or data about which reservoirs have been or have yet to be activated to release the drug therefrom or to expose the sensor therein.

2. The method of claim 1, further comprising using a microprocessor to compare the data transmitted to the remote controller with safety protocols stored in a memory.

3. The method of claim 2, wherein the reservoirs comprise at least one drug for release and the safety protocols prohibit (i) the release of an unsafe quantity of the drug to the patient over a particular time interval, and/or (ii) the unsafe release of two or more incompatible drugs.

4. The method of claim 1, further comprising transmitting the data received by the remote controller to the patient's physician or to a central monitoring system on a real-time basis.

5. The method of claim 1, wherein the data is transmitted in the form of electromagnetic energy selected from radio frequency signals, microwave signals, infrared signals, ultraviolet signals, and combinations thereof.

6. The method of claim 1, wherein the actuation electronics comprises components selected from the group consisting of multiplexers, demultiplexers, signal generators, signal oscillators, amplifiers, switches, potentiostats, and combinations thereof.

7. A method for monitoring the status of a medical device implanted in a patient, the method comprising:
   implanting at a site in a patient a medical device which comprises (i) a substrate in which two or more reservoirs are located, with each covered by a reservoir cap, (ii) a drug formulation disposed in the two or more reservoirs, (iii) a power source and actuation electronics operable to melt each reservoir cap, thereby permitting the drug to be released from the medical device to the patient, and (iv) a telemetry system; and
   using said telemetry system to wirelessly transmit to a remote controller data about the condition of the power source and/or data about which reservoirs caps have been or have yet to be disintegrated, melted, or otherwise ruptured.

8. The method of claim 7, wherein the drug formulation comprises a hormone, steroid, or chemotherapeutic agent.

9. A method for monitoring a medical device implanted in a patient, the method comprising:
   implanting in a patient a medical device which comprises (i) a silicon substrate in which two or more reservoirs are located, with each covered by a reservoir cap comprising a metal film, (ii) a drug or sensor located in the reservoir, (iii) a power source and actuation electronics operable to cause a rise in temperature of each reservoir cap to disintegrate or melt each reservoir cap and thereby expose the drug or sensor to an environment at the site of implantation in the patient, and (iv) a telemetry system; and
   using said telemetry system to wirelessly transmit to a remote controller data about the condition of the power source and/or data about which reservoirs have been or have yet to be activated to release the drug therefrom or to expose the sensor therein.

* * * * *